(12) United States Patent
Kim

(10) Patent No.: US 10,568,618 B2
(45) Date of Patent: Feb. 25, 2020

(54) SURGICAL SUTURE FOR LAPAROSCOPIC PORT SITE CLOSURE DEVICE

(71) Applicant: Ki Seong Kim, Gyeonggi-do (KR)

(72) Inventor: Ki Seong Kim, Gyeonggi-do (KR)

(73) Assignee: Ki Seong Kim, Gyeonggi-do (KR)

( * ) Notice: Subject to any disclaimer, the term of this patent is extended or adjusted under 35 U.S.C. 154(b) by 40 days.

(21) Appl. No.: 15/104,198

(22) PCT Filed: Aug. 31, 2015

(86) PCT No.: PCT/KR2015/009110
§ 371 (c)(1),
(2) Date: Jun. 13, 2016

(87) PCT Pub. No.: WO2016/080640
PCT Pub. Date: May 26, 2016

(65) Prior Publication Data
US 2017/0245852 A1    Aug. 31, 2017

(30) Foreign Application Priority Data

Nov. 21, 2014 (KR) ........................ 10-2014-0163453

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0482* (2013.01); *A61B 17/0483* (2013.01);
(Continued)

(58) Field of Classification Search
CPC .......... A61B 17/06166; A61B 17/0469; A61B 17/0482; A61B 17/0483; A61B 17/04
See application file for complete search history.

(56) References Cited

U.S. PATENT DOCUMENTS 5,454,834 A * 10/1995 Boebel ............. A61B 17/06166
606/228
5,902,312 A * 5/1999 Frater .............. A61B 17/07207
606/148

(Continued)

FOREIGN PATENT DOCUMENTS

JP    2003-093394    4/2003
JP    2009-279464    12/2009

(Continued)

*Primary Examiner* — Richard G Louis
(74) *Attorney, Agent, or Firm* — IP & T Group LLP

(57) ABSTRACT

A surgical suture is caught in a needle tip that is pierced through a body tissue; and when the needle is withdrawn, the surgical suture is pulled out along a path through which the needle was pierced into the tissue, and the surgical suture is tied outside a patient's body. The surgical suture for the laparoscopic port site closure device, wherein the laparoscopic port site closure device is in a tube shape for being introduced into a port site, includes: a tubular body provided with needle guides that face each other and guide insertion of a needle; wings mounted to a lower portion of the tubular body such that the wings are opened and closed through a cam method; and an operating stick penetrating through the tubular body to operate the wings to be opened and to be closed.

4 Claims, 14 Drawing Sheets

(52) U.S. Cl.
CPC .... *A61B 17/0485* (2013.01); *A61B 17/06166* (2013.01); *A61B 17/06109* (2013.01); *A61B 2017/00349* (2013.01); *A61B 2017/00637* (2013.01); *A61B 2017/00663* (2013.01); *A61B 2017/0496* (2013.01); *A61B 2017/06042* (2013.01); *A61B 2017/06176* (2013.01)

(56) References Cited

U.S. PATENT DOCUMENTS

| | | | | |
|---|---|---|---|---|
| 5,964,773 | A * | 10/1999 | Greenstein | A61B 17/0469 606/144 |
| 2005/0251209 | A1* | 11/2005 | Saadat | A61B 17/0401 606/232 |
| 2007/0203507 | A1* | 8/2007 | McLaughlin | A61B 17/0057 606/144 |

FOREIGN PATENT DOCUMENTS

| | | |
|---|---|---|
| JP | 2012-515020 | 7/2012 |
| JP | 2014-511205 | 5/2014 |
| WO | WO 2010/081096 | 7/2010 |

* cited by examiner

SURGICAL SUTURE FOR LAPAROSCOPIC PORT SITE CLOSURE DEVICE

This application is a national stage application of PCT/KR2015/009110 filed on Aug. 31, 2015, which claims priority of Korean patent application number 10-2014-0163453 filed on Nov. 21, 2014. The disclosure of each of the foregoing applications is incorporated herein by reference in its entirety.

TECHNICAL FIELD

The present invention relates generally to a laparoscopic port site closure device. More particularly, the present invention relates to surgical suture for a laparoscopic port site closure device configured such that a cartridge receiving a surgical suture therein is provided at a fore-end of a needle guide for port site closure; the surgical suture is caught in a needle tip that is pierced through a body tissue by being guided by the needle guide; and when the needle is withdrawn, the surgical suture is pulled out along a path through which the needle is pierced into the tissue, and the surgical suture is tied outside a patient's body, thereby being capable of closing a laparoscopic port site.

BACKGROUND ART

In general, laparoscopic surgery, unlike conventional open surgical procedures, refers to a surgical technique where four to six incisions about 0.5~1.2 cm in size are made on the patient's abdomen, and trocars, which have a diameter of 0.5~1.2 cm and are 15~16 cm long, are placed through these incisions. A light source, a camera, and surgical instruments are then introduced into the abdomen through the trocars. The surgeon performs the procedure, watching a television monitor on which the camera transmits an image of the organs inside the abdomen.

Laparoscopic surgery is used for cholecystectomy, bile duct stone removal, hepatic duct stone removal, appendectomy, and removal of tumors in a variety of organs. Patients with laparoscopic surgery have much less pain, fewer complications such as enteroplegia, shorter hospital stay, rapid recovery, and less post-operative scarring compared to patients with open surgical procedures.

For laparoscopic surgery, after a plurality of trocars is placed into a patient's abdomen, carbon dioxide gas is used to inflate the abdomen through one of the trocars in order to give the surgeon room to work. The endoscope and surgical instruments are then introduced through other trocars. The surgeon performs a surgery for the affected area, monitoring the surgical site.

After the procedure, in order to close the incisions, a trocar site closure tool is used. The trocar site closure tool is configured such that the incisions are closed by stitching while the needle is held by the forceps that are placed into the abdominal cavity through the trocar. After closing the incisions, in order to prevent the stitches from being untied, opposite ends of the surgical suture are pulled out of the patient's body through the trocar, and the knots are tied outside the patient's body. After tying the knots, the knots are formed into the abdominal cavity by pushing the knots using a compressor.

However, the conventional trocar site closure tool for laparoscopic surgery described above is problematic in that when the surgical suture, which is pulled out through the incision along with the needle, is pulled using the forceps, the surgical suture may be easily cut by the pressure of the forceps.

Further, after stitching the incisions, to prevent the stitches from being untied, the knots are tied. When opposite ends of the surgical suture are pulled out of the patient's body in order to tie the knots, an additional instrument, such as forceps or pincette, is required.

As another related art, a fascial closure device is shown in FIG. 1.

The fascial closure device, which is in a tube shape for being introduced into a port site, includes: a tubular body 1 formed with needle guides 2 that face each other and guide insertion of a needle 3; and a pair of wings 5 being mounted to a lower portion of the tubular body 1, and being opened and closed using cam method, wherein each of the wings 5 is provided with a silicon pad 6 at a location where the needle 3 penetrates through, and the wings 5 are configured to be opened by rotating an operating stick 4 and configured to be closed by reversely rotating the operating stick 4.

The conventional fascial closure device solves a few of the above problems occurring in the related art. However, the fascial closure device is still problematic in the closure process. Reference will be made to the closure process using the conventional fascial closure device.

As shown in FIGS. 2 and 3, the needle 3 penetrates through a tissue along the guide path 2 by threading the surgical suture 7. Here, the needle 3 is placed on the silicon pad 6 of the wing 5. When the needle 3 is further pushed into the silicon pad 6, the needle tip penetrates therethrough. After that, when the needle 3 is pulled out, the surgical suture 7 remains compressed in the silicon pad 6.

After the surgical suture 7 is compressed in the silicon pad 6 of the wings 5, the needle 3 is removed. The operating stick 4 is then rotated so as to close the wings 5, whereby the compressed surgical suture 7 is concentrated around the axis of the tubular body 1. When the tubular body 1 is withdrawn, the surgical suture 7 is pulled out and tied, whereby the closure is completed.

However, the conventional fascial closure device is problematic in that the suture area is easily infected by the surgical suture that is placed thereon during the recovery because the surgical suture, which penetrates through a tissue around the port site, is pulled out of a patient's body through the port.

Further, the conventional fascial closure device requires cutting the surgical suture into a predetermined length and threading the needle with the surgical suture. Thus, the procedure is inconvenient. The conventional fascial closure device is further problematic in that when the binding force of the silicon pad to the surgical suture becomes weak, it is difficult to pull out the surgical suture, thereby requiring additional work.

Further, in the process of threading the surgical suture in the needle, a surgeon or a nurse may be stuck or infected by the needle. In the process of closing a plurality of ports, the above mentioned problems occur repeatedly, whereby the operation time may be long.

DISCLOSURE

Technical Problem

Accordingly, the present invention has been made keeping in mind the above problems occurring in the related art, and the present invention is intended to propose surgical suture.

The present invention is configured such that a tubular body of the laparoscopic port site closure device is provided with a detachable cartridge at an end thereof so as to be capable of being repeatedly used by replacing only the cartridge. Thus, the surgical suture according to the present invention is convenient and kept free from spreading infection.

The present invention is configured such that the cartridge includes wings capable of being open enough to fit a location where a needle is inserted; and the surgical suture being received therein, the surgical suture temporarily locked to the wings. Thus, the surgical suture according to the present invention does not require tying the surgical suture, whereby it is possible to realize speedy closure.

The present invention is configured such that the surgical suture, which is placed in the abdominal cavity, is simply pulled out of a patient's body in order to close an opening the tissue. Thus, the surgical suture according to the present invention prevents an incision area, namely an opening port site, from intervention of the surgical suture therein.

The present invention includes a needle for catching and withdrawing the surgical suture that is placed in the abdominal cavity. Thus, the surgical suture according to the present invention prevents the surgical suture from slipping off from the needle.

The present invention is configured such that the surgical suture that is received in the laparoscopic port site closure device is provided with an additional structure at opposite ends thereof so as to be caught and pulled out using the needle. Thus, the surgical suture according to the present invention realizes easy closure of an incision site.

The present invention is configured such that the cartridge, in which the surgical suture is received, is replaceable. Thus, the present invention is capable of allowing a port site closure device to be reused by replacing the cartridge, thereby economical.

Technical Solution

In order to achieve the above object, according to one aspect of the present invention, there is provided a surgical suture for a laparoscopic port site closure device.

The surgical suture for the laparoscopic port site closure device, which is in a tube shape for being introduced into a port site, includes: a tubular body provided with needle guides that face each other and guide insertion of a needle; wings mounted to a lower portion of the tubular body such that the wings are opened and closed through a cam method; and an operating stick penetrating through the tubular body to operate the wings by being rotated to push and open the wings and to pull and close the wings by being rotated reversely. The laparoscopic port site closure device further includes: a replaceable cartridge provided on a lower end of the tubular body to be detachably combined with the operating stick, wherein the cartridge is provided with the wings capable of being opened by operating the operating stick, and provided with a compartment for receiving surgical suture therein, wherein the laparoscopic port site closure device is configured such that opposites ends of the surgical suture in the compartment are threaded through the wings such that the ends of the surgical suture are pulled out of a patient's body by being caught by a suture slot of a needle that is pierced into the patient's body from outside.

The needle may include a suture slot for catching and pulling out surgical suture by being concavely formed on a needle tip in an opposite direction of pulling the surgical suture.

The surgical suture may be received at a lower end of the cartridge, wherein each end of the surgical suture may be provided with a spiral coil, with a stopper provided at each end of the coil, such that the surgical suture is easily caught in the suture slot. Herein, the surgical suture is folded and received in a case to be easily unfolded toward outside when being pulled out of the case.

Attachment and detachment of the cartridge and operation of the wings that are provided in the cartridge may be dependent on a location of the operating stick. To achieve this, the device may be provided with protrusions and grooves.

Advantageous Effects

According to the present invention having the above-described characteristics, the advantageous effects of the present invention are as follows. The present invention is configured such that a tubular body of the laparoscopic port site closure device is provided with a detachable cartridge at an end thereof so as to be capable of being repeatedly used by replacing only the cartridge. Thus, the present invention is convenient and kept free from transmitting infection. The present invention is further configured such that the cartridge includes wings capable of being open enough to fit a location where a needle is inserted; and surgical suture being received therein, the surgical suture temporarily locked to the wings. Thus, the laparoscopic port site closure device according to the present invention does not require tying the surgical suture, whereby it is possible to realize speedy closure of an incision site. The present invention is further configured such that the surgical suture, which is placed in the abdominal cavity, is simply pulled out of a patient's body in order to close an opening in the tissue. Thus, the laparoscopic port site closure device according to the present invention prevents an incision area, namely an opening port site, from intervention of the surgical suture therein, thereby realizing speedy recovery. The present invention includes a needle for catching and withdrawing the surgical suture that is placed in the abdominal cavity. Thus, the laparoscopic port site closure device according to the present invention prevents the surgical suture from slipping off the needle, thereby realizing speedy and safe procedure.

The present invention is configured such that the surgical suture that is receive in the laparoscopic port site closure device is provided with an additional structure at opposite ends thereof so as to be caught and pulled out using the needle. Thus, the laparoscopic port site closure device according to the present invention realizes easy closure of an incision site. The present invention is configured such that the cartridge, in which the surgical suture is received, is replaceable. Thus, the laparoscopic port site closure device according to the present invention is capable of being used repeatedly and is thereby economical.

DESCRIPTION OF DRAWINGS

FIG. 4b is a partial exploded perspective view of FIG. 4a;

BEST MODE

Figure 1:
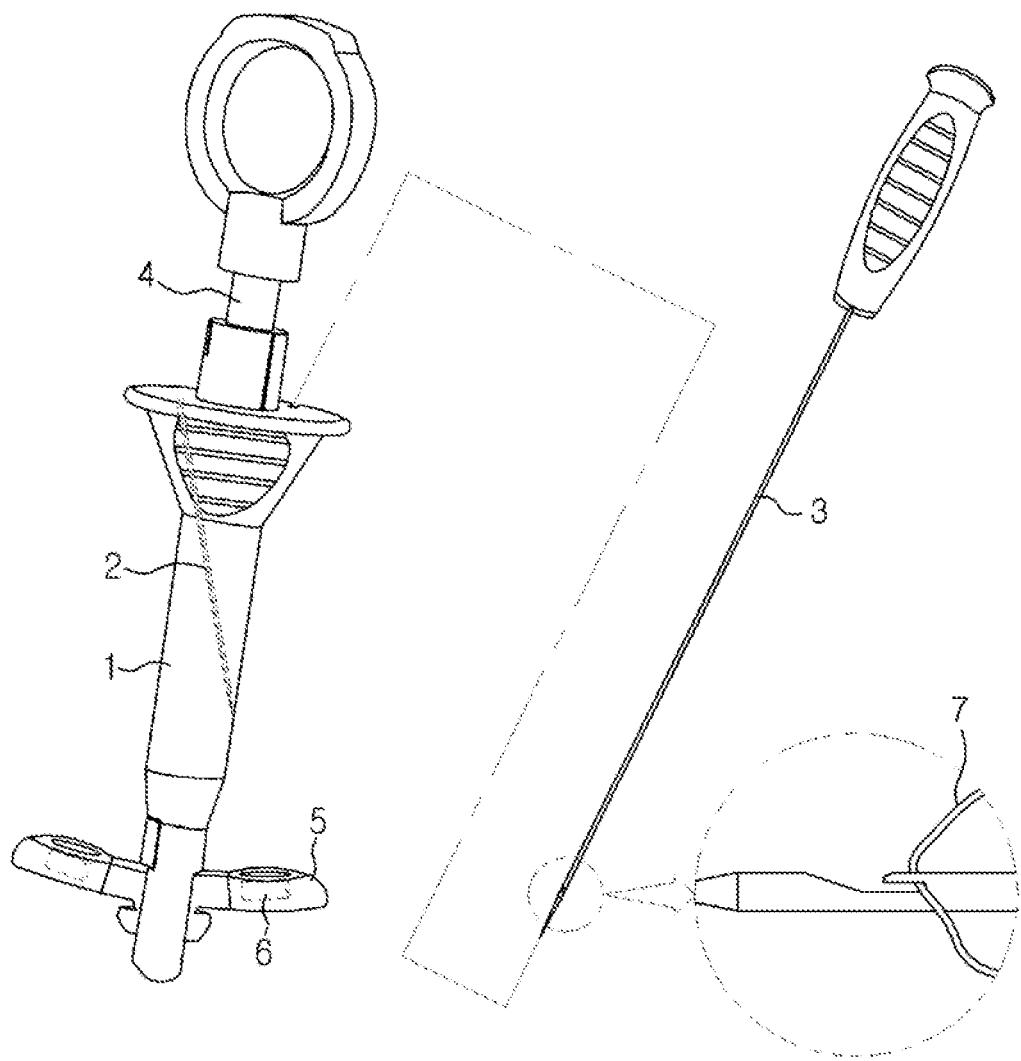
FIG. 1 is a view illustrating a conventional laparoscopic port site closure device.
Figure 2A:
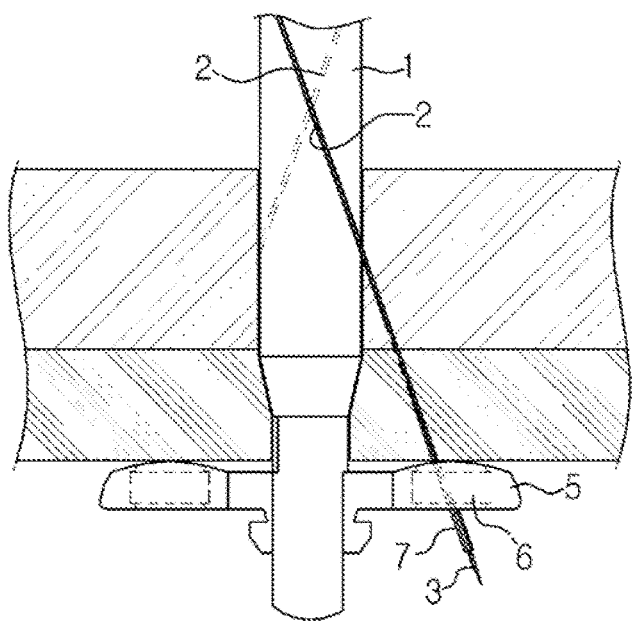
FIGS. 2a and 2b are sectional views of essential portions illustrating a closure process using the device of FIG. 1.
Figure 2B:
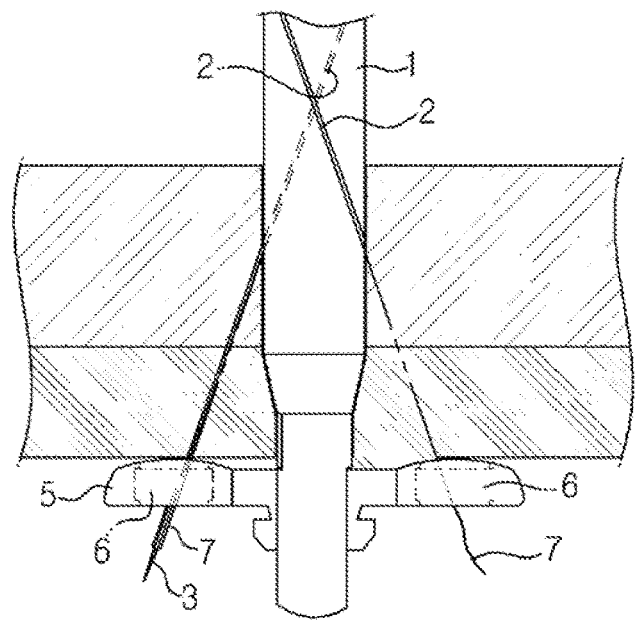
Figure 3:
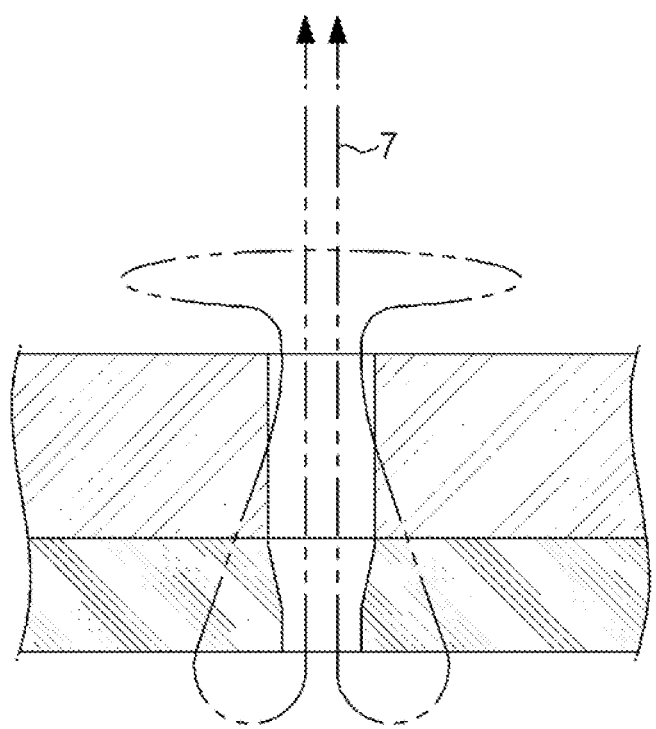
FIG. 3 is a schematic view illustrating a final tie structure of surgical suture in the closure process of FIG. 1.
Figure 4A:
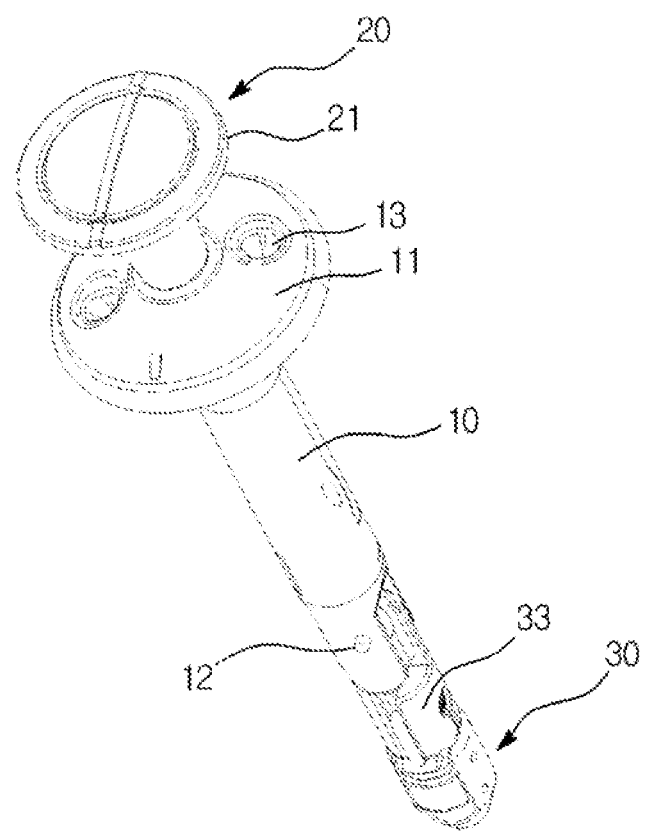
FIG. 4a is a perspective view illustrating an appearance of a laparoscopic port site closure device to which the present invention is applied.
Figure 4B:
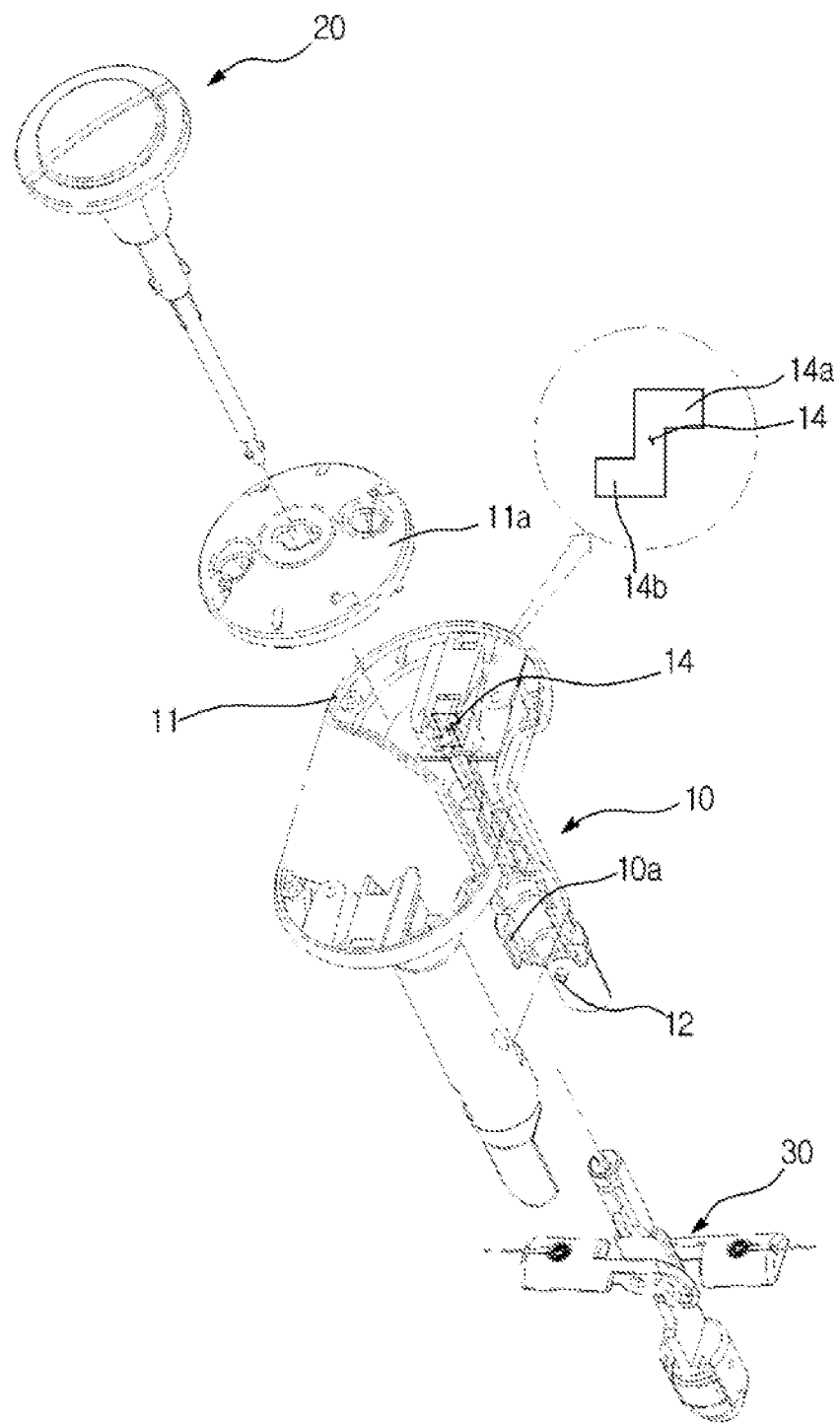

Reference will now be made in greater detail to an exemplary embodiment of the present invention, an example of which is illustrated in the accompanying drawings. Wherever possible, the same reference numerals will be used throughout the drawings and the description to refer to the same or like parts.

As shown in FIGS. 4 to 7, a laparoscopic port site closure device according to the present invention, which is in a tube shape for being introduced into a port site, includes: a tubular body provided with needle guides that face each other and guide insertion of a needle; wings mounted to a lower portion of the tubular body such that the wings are opened and closed through a cam method; and an operating stick penetrating through the tubular body to operate the wings by being rotated to push and open the wings and to pull and close the wings by being rotated reversely. The laparoscopic port site closure device further includes: a replaceable cartridge 30 provided on a lower end of the tubular body 10 to be detachably combined with the operating stick 20, wherein the cartridge 30 is provided with the wings 33 capable of being opened by operating the operating stick, and provided with a compartment 32 for receiving surgical suture 40 therein, wherein the laparoscopic port site closure device is configured such that opposites ends of the surgical suture 40 in the compartment are threaded through the wings 33 such that the ends of the surgical suture are pulled out of a patient's body by being caught by a suture slot of a needle 50 that is pierced into the patient's body from outside.

The tubular body 10 that is divided into two parts may include a cone-shaped handle 11 and a tube that extends from the handle; inner protrusions 12 that face each other are provided inside of the tube at a lower portion thereof; needle guide holes 13 that are disposed opposite to each other and range from an upper portion of the handle 11 to a side wall of the tube are provided on the handle 11 for guiding introduction and withdrawal of the needle; and a guide groove 14 is provided inside the handle 11 and guides a rotation and forward-backward movement of the operating stick 20 and fixes a location of the operating stick.

The guide groove 14 is provided in each half of the tubular body, wherein the guide groove 14 includes an inward groove and an outward groove 14a and 14b so as to form the crank shaped guide groove 14.

The operating stick 20 may include a handle 21 and a rod that extends from the handle, wherein outer protrusions 22 that are disposed opposite to each other are provided at an end of the rod, and guide protrusions 23 that are disposed opposite to each other are provided below the handle 21 by protruding and serve to mount and demount the cartridge 30 such that the cartridge is combined with the tubular body 10.

The cartridge 30 may include: a first support 300 including a mounting slot 301 provided in the center thereof, and locking channels 302 disposed opposite to each other provided on an outer circumferential surface thereof; a second support 310 provided beneath the first support, the second support being in a planar shape so as to support a surface of each of the wings 33, and including wing protrusions 311 disposed opposite to each other as a pivot of the wings; a third support 320 being in a planar shape rotated at an angle of 90 degrees relative to the second support, having a width to come into close contact with the wings 33 when the wings are closed, and including the compartment 32 that is in a cone shape and is provided at a lowermost end thereof and a cover 322 for covering the compartment; and the wings 33 each including: a wing hole 331 for being engaged with the wing protrusions 311 of the second support 310; an arch-shaped link hole 333 that is provided outside the wing hole 331, the link hole 333 having an opening at an edge thereof with a ridge 334 provided by protruding in the opening; a mounting hole 335 for mounting an end of the surgical suture 40; and a communication slot 336 provided on an outer surface of the wing to communicate with the mounting hole 335, wherein the wings comprise a pair of wings that are disposed opposite to each other.

When the cartridge 30 including the wings 33 is assembled with the tubular body, the cartridge may share the same center point as the tubular body and may have no protruding surfaces.

The compartment 32 may include a notch 337 provided at a portion of an outer surface thereof so as to serve as a suture outlet for the surgical suture that is received therein.

The surgical suture 40 may be received at a lower end of the cartridge 30, wherein each end of the surgical suture 40 may be provided with a spiral coil 42, with a stopper 43 provided at each end of the coil, such that the surgical suture is easily caught in the suture slot. Herein, the surgical suture is folded and received in a case 45 to be easily unfolded toward outside when being pulled out of the case.

Further, the spiral coil 42 that is combined with the surgical suture may be provided with a silicon tube 46 fitted over a junction between the spiral coil and the surgical suture.

An end of the coil, which is made of metal, may be melted to form a ball-shaped stopper 43.

The spiral coil 42 may be made of a metal wire having a diameter of 0.1~0.15 mm by coiling the metal wire such that the coil is extended when pulled by an external force.

The needle 50 may be long enough to reach from the needle guide holes 13 to the wings 33 that are opened, and the needle 50 may be provided with a suture slot 52 at a tip thereof by being concavely formed thereon.

In other words, the suture slot 52 of the needle 50 may be concavely formed on a needle tip in an opposite direction of pulling the surgical suture so as to catch and pull out the surgical suture.

Reference numeral 11*a* denotes a handle cover of the tubular body for allowing easily recognizing a lock or an unlock state of the operating stick 20, and reference numeral 10*a* denotes a locking clip for assembling the tubular body that is divided into two parts.

Reference will now be made in greater detail to operation of the surgical suture for the laparoscopic port site closure device, hereinbelow.

The surgical suture according to the present invention may be configured such that the surgical suture 40, which is in the case 45, is received in the compartment 32, and the coil 42 provided at each end of the surgical suture is inserted into the mounting hole 335 of the wings 33, wherein the surgical suture is pulled out through the notch 337 of the compartment 32.

Here, the silicon tube 46 of the surgical suture may be made of a soft material so as to be deformed to help the surgical suture to be caught in the communication slot 336 for temporal fixation. Further, the silicon tube 46 covers and protects the junction between the spiral coil and the surgical suture, wherein the surgical suture is combined with the end of the coil 42.

When the cartridge 30 that receives the surgical suture is inserted into the tubular body 10, the inner protrusions 12 at the lower portion of the tubular body are combined with the cartridge 30 by passing the ridge 334 of each of the wings 33. Here, the outer protrusions 22 of the operating stick 20 are guided to and mounted to the mounting slot 301 of the first support 300.

When the laparoscopic port site closure device according to the present invention is used to close the port site, as a manner similar to a conventional operation, after a cone-shaped fore-end of the cartridge 30 is inserted into the patient's body by holding the cone-shaped handle 11 according to the present invention, the link hole 333 is engaged with the inner protrusions 12 around the wing protrusions 311 by pulling the handle 21 of the operating stick 20, wherein the wings 33 that are combined with the wing protrusions 311 of the second support 310. Here, when the operating stick 20 is rotated at an angel of 45 degrees clockwise, the wings 33 are opened along an edge of the arch-shaped link hole.

The opened wings 33 may be perpendicular to the tubular body, and an angle of rotation is dependent on the link hole.

Figure 10:
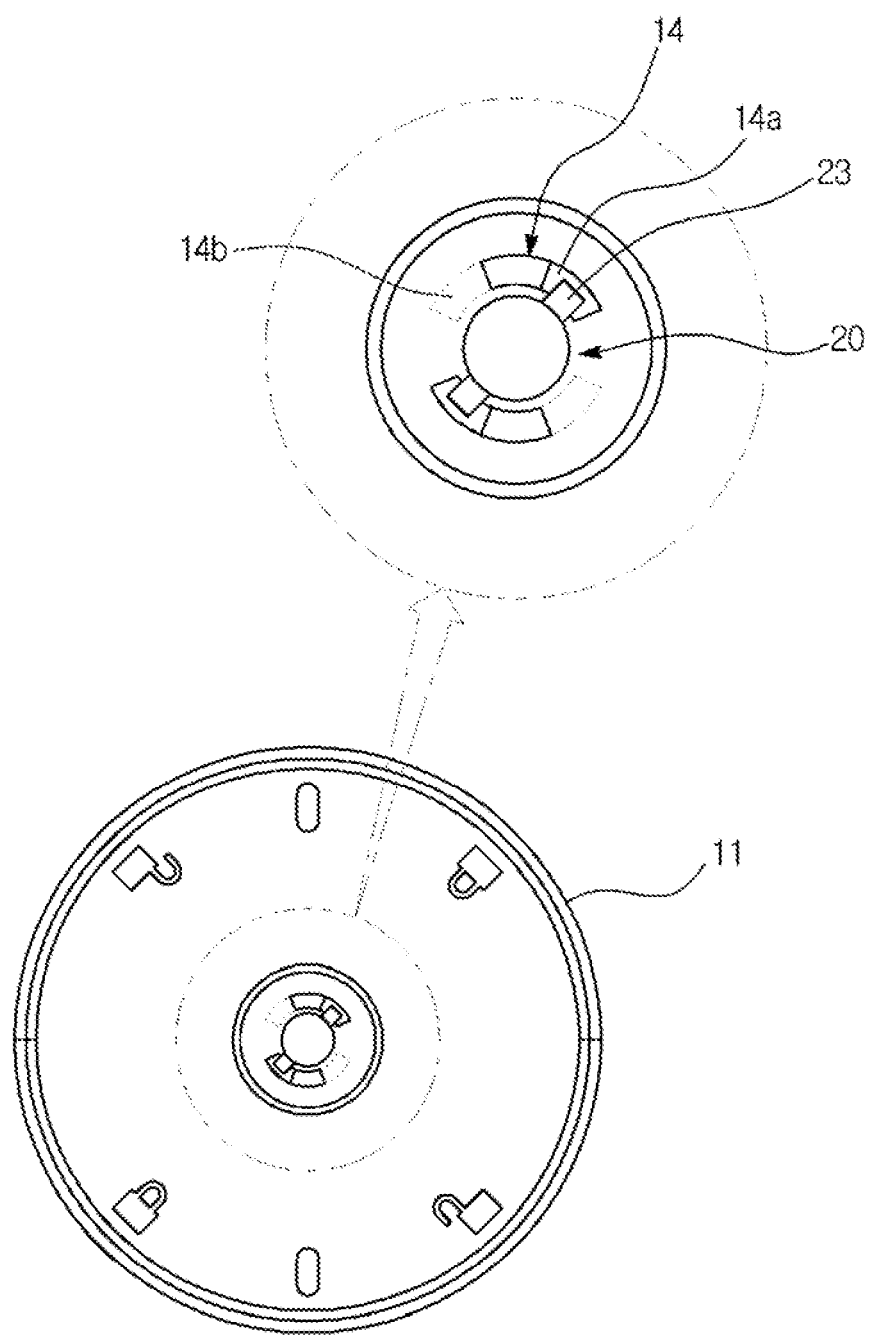

The guide protrusions 23 of the operating stick 20 are engaged with the inward groove 14*a* of the guide groove 14 such that a location of the operating stick 20 is fixed, whereby the opened wings 33 remain open (see FIG. 10).

The guide groove 14 is crank shaped and includes grooves 14*a* and 14*b* for guiding a rotation and forward-backward movement of the operating stick 20 and fixing a location of the operating stick.

Figure 5:
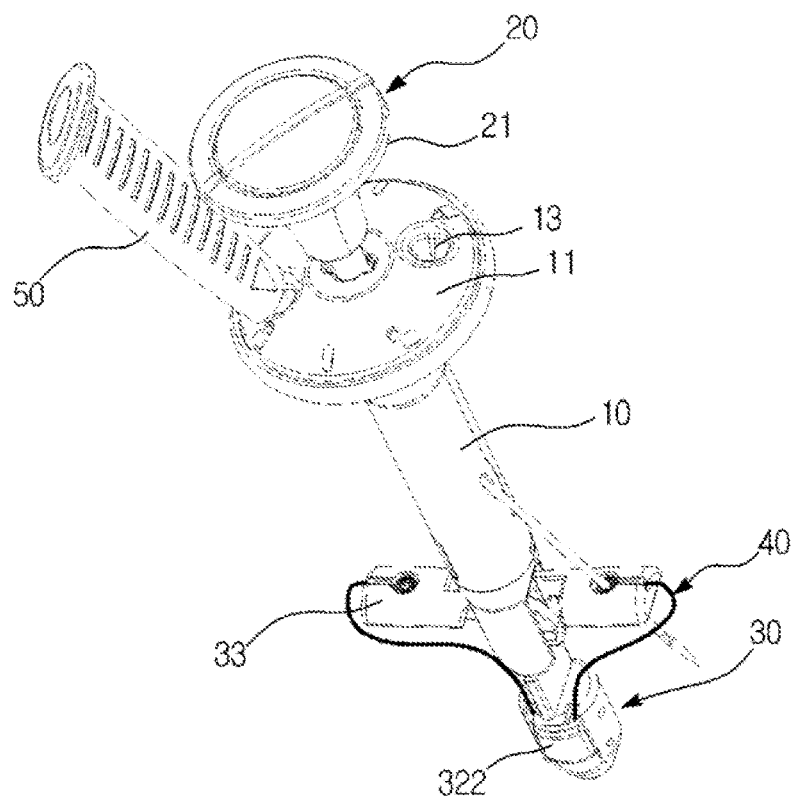
FIG. 5 is a perspective view of the laparoscopic port site closure device, to which the present invention is applied, illustrating a state where a needle is inserted into a wing by opening the wing.
Figure 6:
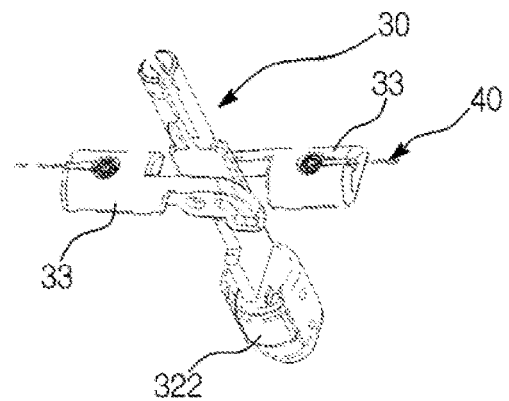
FIG. 6 is a view illustrating a cartridge of the laparoscopic port site closure device to which the present invention is applied.
Figure 7:
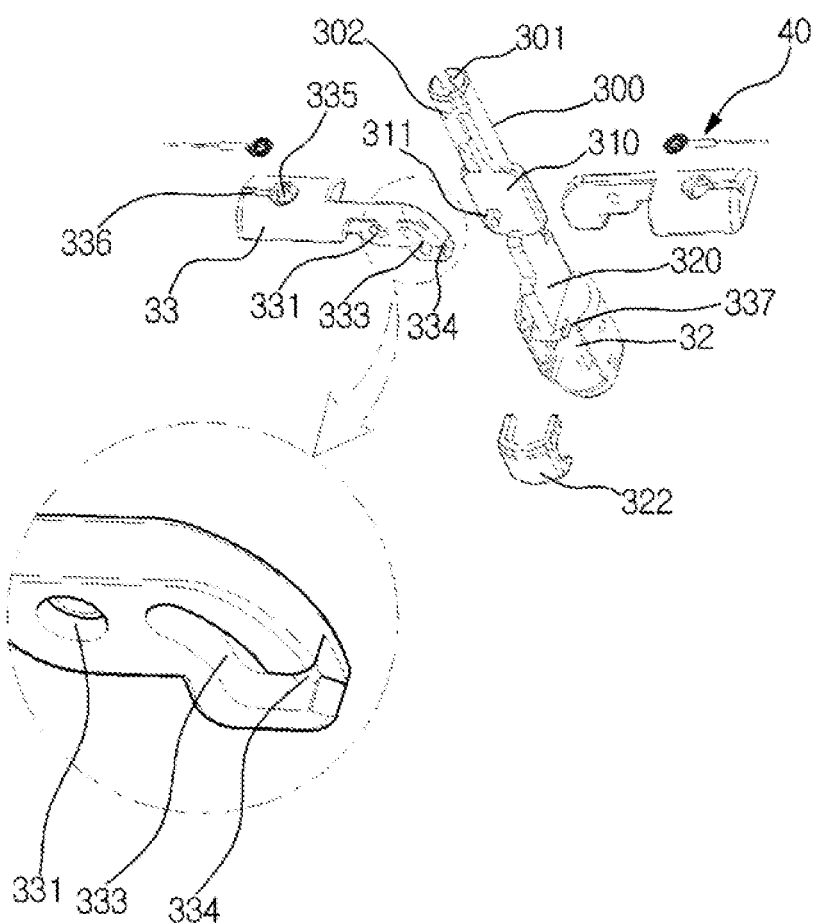
FIG. 7 is an exploded perspective view illustrating the cartridge of the laparoscopic port site closure device to which the present invention is applied.
Figure 8:
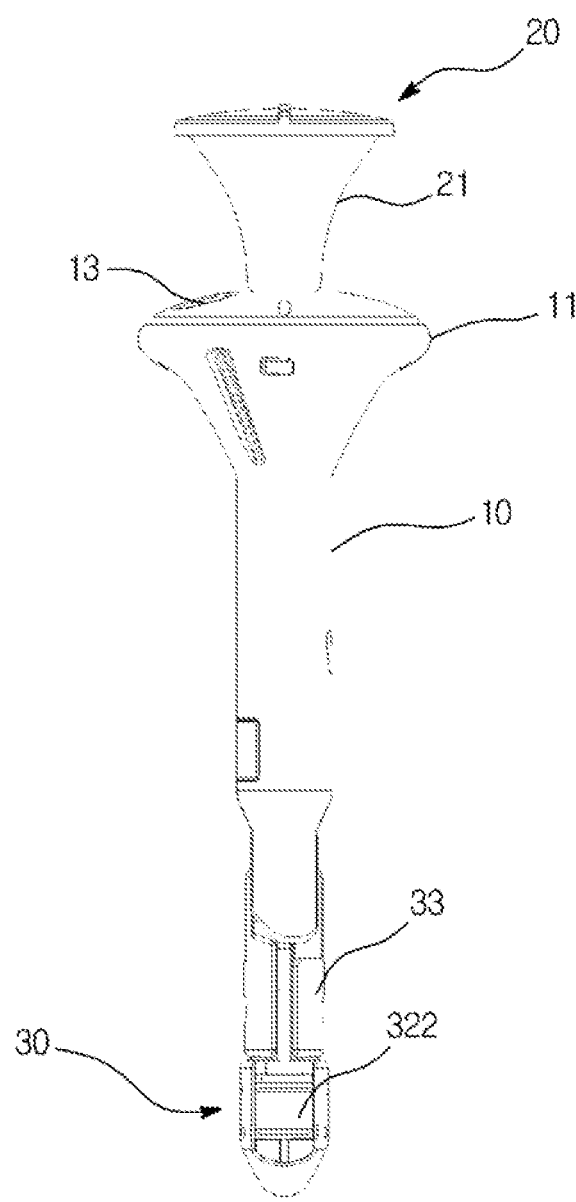
FIG. 8 is a view illustrating a configuration of an operating stick that operates the cartridge of the laparoscopic port site closure device to which the present invention is applied.
Figure 15:
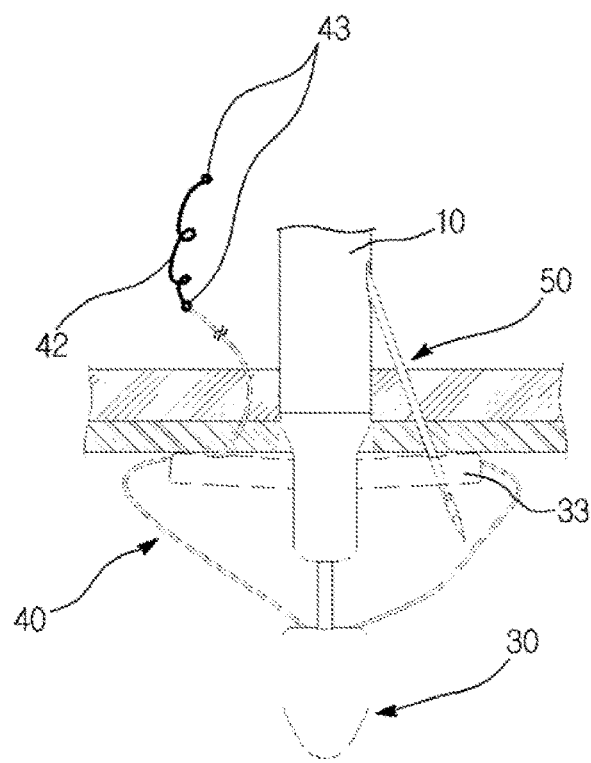
FIG. 15 is a schematic view illustrating a closure process using of the laparoscopic port site closure device to which the present invention is applied.
Figure 16:
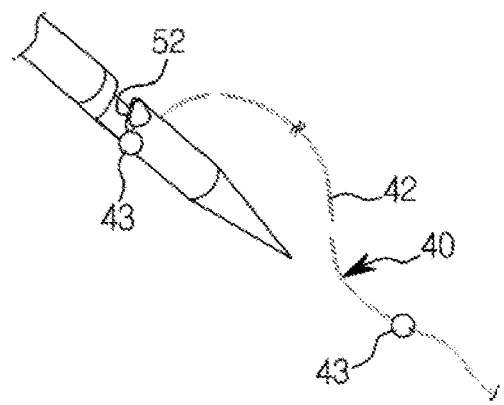
FIG. 16 is a schematic view illustrating a state where the surgical suture is caught in the needle according to the present invention.

After the wings 33 is opened and fixed, as shown in FIG. 5, when the needle 50 is inserted through the guide holes 13, the needle tip is pierced through a tissue around a port. The needle is then withdrawn after the coil 42 is passed through the wings 33. Here, the stopper 43 of the coil is caught in the suture slot 52 of the needle, wherein the coil is extended along the needle that is pulled, whereby a tied portion of the surgical suture is safely pulled out of the patient's body (see FIGS. 15 and 16).

Figure 9:
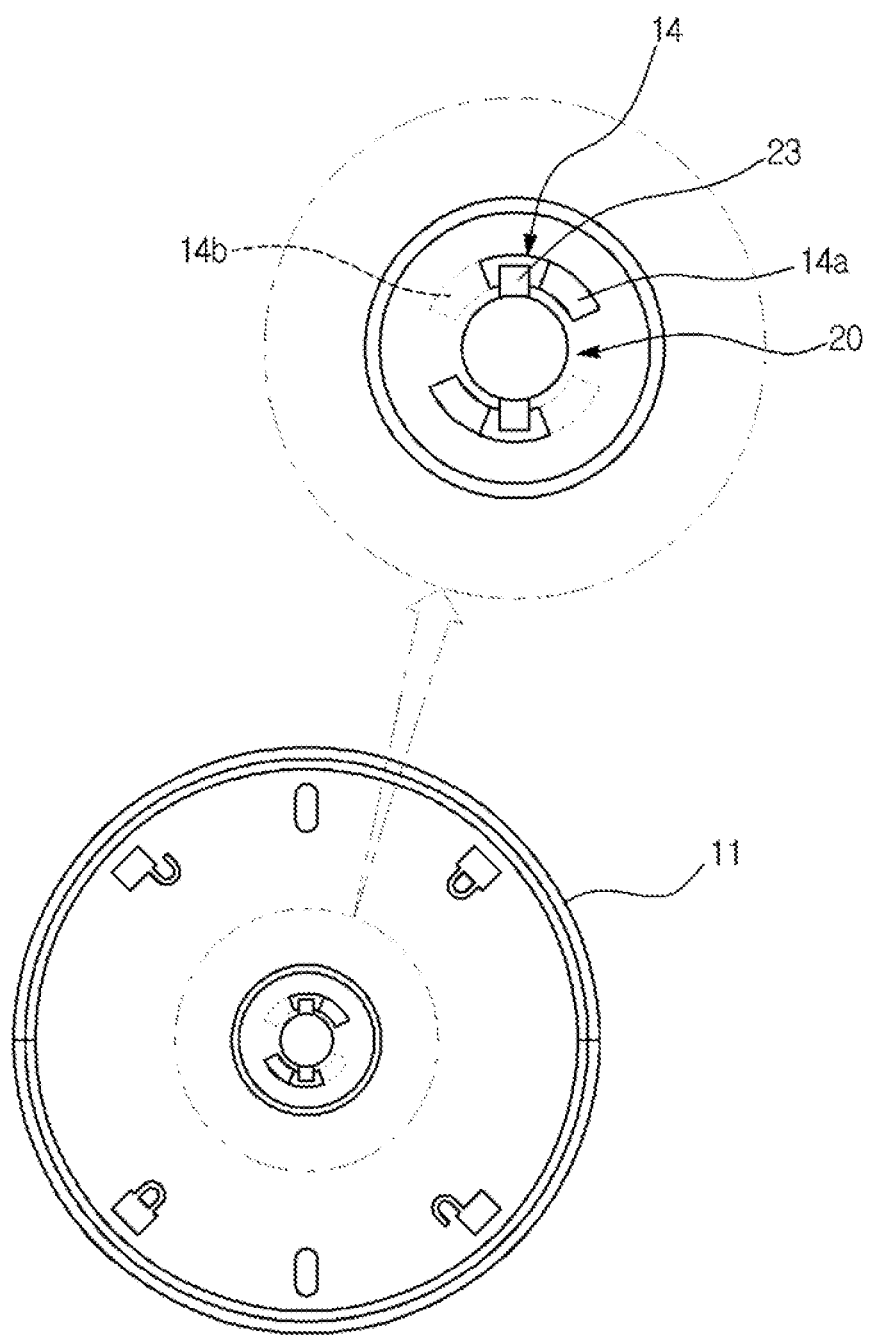
FIGS. 9 to 12 are views illustrating operation of the cartridge in response to manipulation of the operating stick of the laparoscopic port site closure device to which the present invention is applied.
Figure 17:
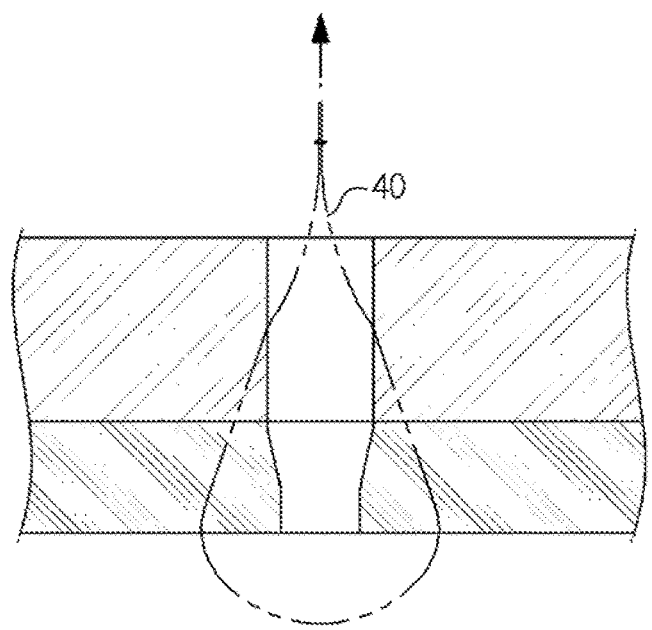
FIG. 17 is a schematic view illustrating a state of a port site being finally sutured by the surgical suture according to the present invention.

As shown in FIG. 9, after opposite ends of the surgical suture 40 are pulled out of the patient's body, when the operating stick 20 is rotated at an angel of 45 degrees clockwise, the guide protrusions 23 engaged with the inward groove 14*a* of the guide groove 14 are disengaged. When the operating stick 20 is then pushed, the opened wings 33 are closed. When the cone-shaped handle 11 is pulled out, the entire tubular body 10 of the laparoscopic port site closure device comes out of the patient's body. Here, the surgical suture is tied using the conventional suturing method, and the coil is removed (see FIG. 17).

As shown in FIG. 9, after opposite ends of the surgical suture 40 are pulled out of the patient's body, when the operating stick 20 is rotated at an angel of 45 degrees counterclockwise, the guide protrusions 23 engaged with the inward groove 14*a* of the guide groove 14 are disengaged. When the operating stick 20 is then pushed, the opened wings 33 are closed. When the cone-shaped handle 11 is pulled out, the entire tubular body 10 of the laparoscopic port site closure device comes out of the patient's body. Here, the surgical suture is tied using the conventional suturing method, and the coil is removed (see FIG. 17).

Figure 11:
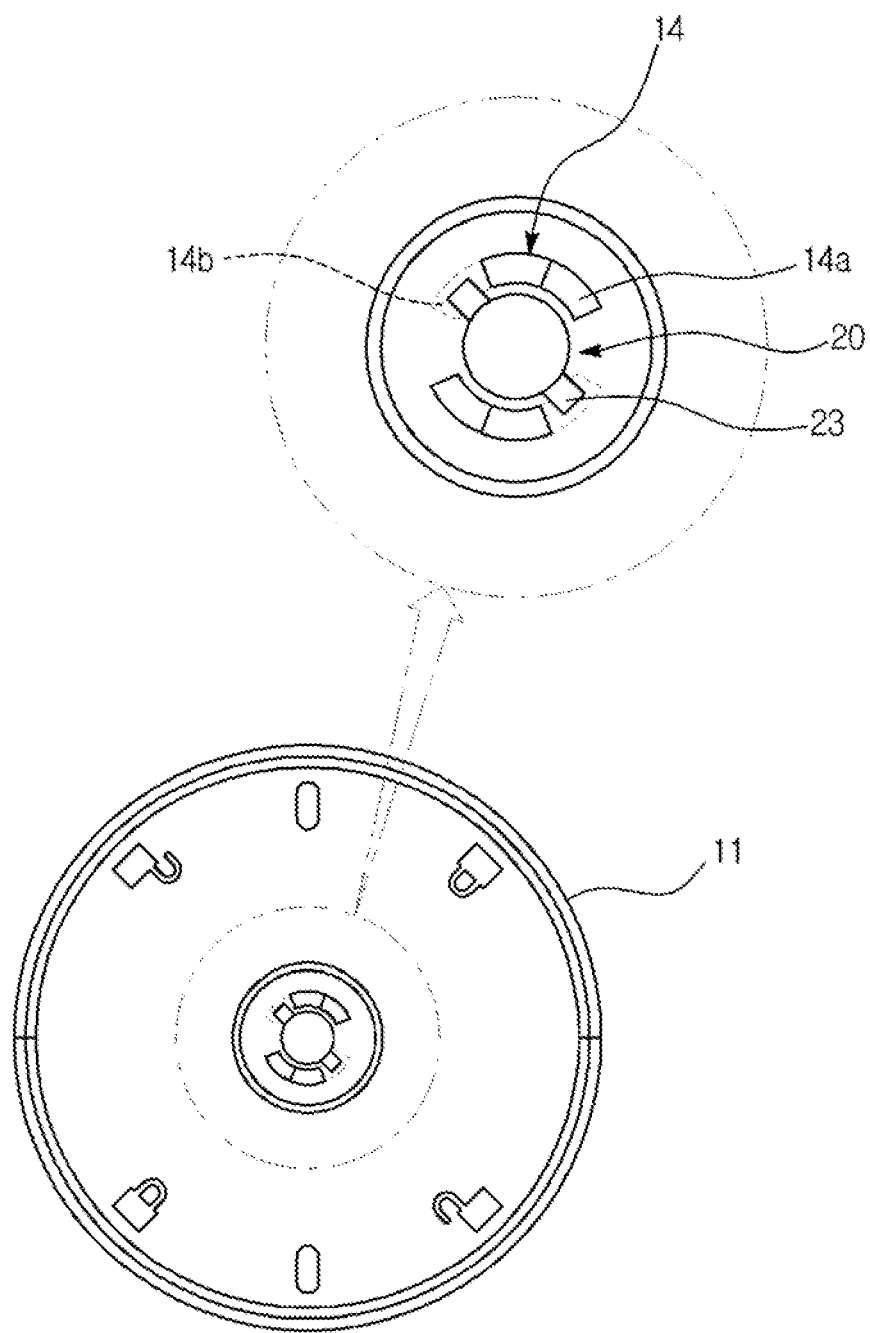
Figure 12:
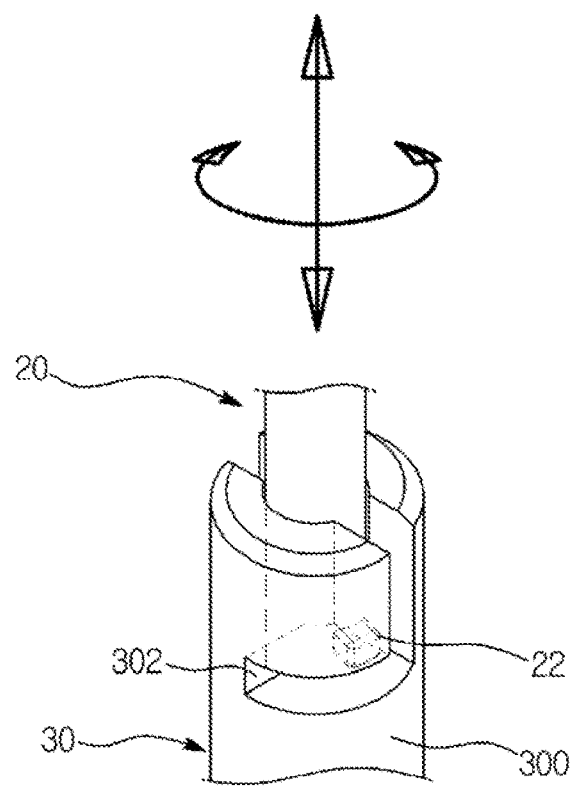
Figure 13:
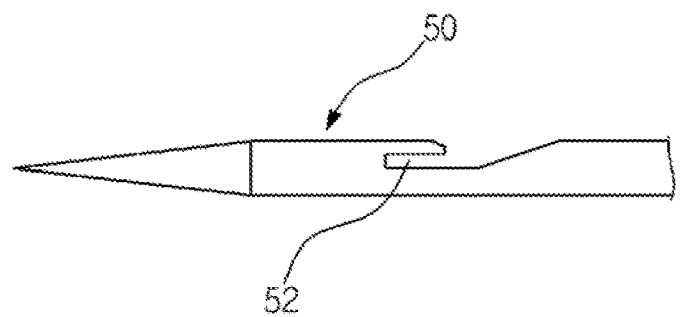
FIG. 13 is a view of an essential portion illustrating a configuration of the needle of the laparoscopic port site closure device to which the present invention is applied.
Figure 14:
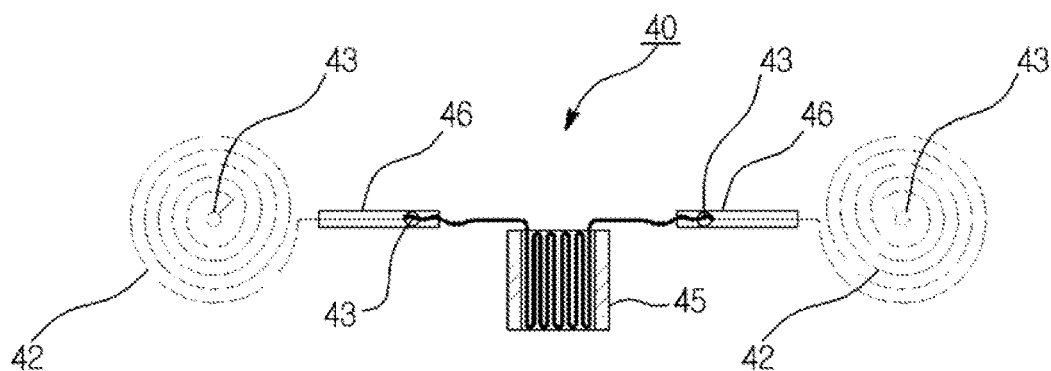
FIG. 14 is a view illustrating a structure of surgical suture according to the present invention.

When the cartridge 30 is replaced after using the laparoscopic port site closure device and the surgical suture therein, as shown in FIG. 11, the operating stick 20 is further rotated at an angel of 45 degrees counterclockwise. Here, the guide protrusions 23 of the operating stick are locked to the outward groove 14*b* of the crank shaped guide groove 14, and the outer protrusions 22 engaged with the locking channels 302 of the cartridge 30 are moved to an unlock location. Thereby, the cartridge 30 is detached from the operating stick 20 (see FIGS. 11 and 12)

The cartridge 30 detached from the operating stick 20 is still combined with the tubular body 10 because the inner protrusions 12 provided inside the tubular body 10 at the lower portion thereof are engaged with the link hole 333 and the ridge 334 of the wings 33. This engagement is configured such that the tubular body 10 is detached from the cartridge 30 by a user's physical force.

A new cartridge 30 is combined with the tubular body 10 in a reverse process so as to reuse the laparoscopic port site closure device.

The needle 50 is configured to catch and pull out the coil 42. Thus, the suture slot 52 for catching the surgical suture is longitudinally formed on the needle tip so as to pull out the surgical suture.

Further, each end of the surgical suture 40 may be provided with the coil so as to easily pull out the surgical suture using the needle, wherein the coil is made of a harmless metal material and is coiled into a spiral shape so as to be easily threaded through the needle. The coil maintains an original shape thereof using elasticity thereof, and the coil is extended by being caught in the needle. Here, a coil having enough elasticity and rigidity to be extended long may be used for the coil. Each end of the coil may be melted to form the ball-shaped stopper 43, whereby it is possible to manufacture a stopper having a simple structure through easy processing.

The stopper 43 of the coil prevents the coil from deviating from the suture slot 52 of the needle, and also prevents the surgical suture from being separated from the coil.

The surgical suture 40 is folded and received in the tubular case, and opposite ends of the surgical suture 40 are threaded through the wings 33 in order to use. The surgical suture may be provided in a state where the surgical suture is received in the cartridge.

The spiral coil 42 is capable of being threaded through the needle tip using a gap between spirals even when the tip of the needle 50 is inserted not perfectly in the middle of the coil. Further, the spiral coil 42 is capable of being threaded through the needle tip using the gap between the spirals regardless of a direction where an opening of the suture slot 52 faces when inserted. Once the coil is caught in the suture slot 52 of the inserted needle tip, the stopper 43 of the coil is caught in the suture slot 52 by being pulled by the needle, thereby extending and being pulled outside. Thus, it is possible to prevent failure in removing the surgical suture.

The present invention is capable of clearly removing the surgical suture when closing a port site, thereby helping the recovery of a patient by lowering the possibility of infection during the recovery. Further, the present invention is capable of realizing an easy procedure by having a handle manipulation structure that allows easy closure of the port site, thereby helping medical staff. Furthermore, the present invention is simple and economical because the cartridge receiving the surgical suture therein is replaceable.

[Description of reference characters of important parts]

| | |
|---|---|
| 10: tubular body | 11: cone-shaped handle |
| 21: handle | 12: inner protrusions |
| 22: outer protrusions | 23: guide protrusions |
| 311: wing protrusions | 13: needle guide holes |
| 14: guide groove | 20: operating stick |
| 30: cartridge | 32: compartment |
| 33: wings | 40: surgical suture |
| 42: coil | 43: stopper |
| 45: case | 46: silicon tube |
| 50: needle | 52: suture slot |
| 300: first support | 301: mounting slot |
| 302: locking channels | 310: second support |
| 320: third support | 322: cover |
| 331: wing hole | 333: link hole |
| 334: ridge | 335: mounting hole |
| 336: communication slot | |

The invention claimed is:

1. A surgical suture system for use with a laparoscopic port site closure device, wherein the laparoscopic port site closure device includes:
   a tubular body;
   wings being opened and closed through a cam method; and
   an operating stick penetrating through the tubular body to operate the wings by being rotated to push and open the wings and to pull and close the wings by being rotated reversely, the laparoscopic port site closure device being configured such that a surgical suture is threaded through the wings so as to pull the surgical suture out of a body of a patient, and wherein
   the surgical suture system comprises:
   the surgical suture which is made of a first material;
   a spiral coil made of a second material that is different from the first material of the surgical suture and which is connected via first and second junctions to each end of the surgical suture, wherein the coil is configured to engage a needle used with the laparoscopic port site closure device so as to be pulled outside of the body of the patient,
   a silicone tube fitted over each of the first and second junctions between the spiral coil and the surgical suture to protect the first and second junctions, and
   a ball-shaped stopper integrally provided at each end of the spiral coil configured to engage the needle and prevent the spiral coil from detaching from the surgical suture;
   wherein the surgical suture is folded and received in a case that is configured to be connected to the laparoscopic port site closure device via a removable cartridge that contains both the case and the spiral coils.

2. The surgical suture of claim 1, wherein the spiral coil is made of a metal wire having a diameter of 0.1~0.15 mm by coiling the metal wire such that the coil is extended when the coil is pulled by an external force.

3. The surgical suture system of claim 1 wherein the spiral coil is made of metal and an end of the coil is melted to form the ball-shaped stopper.

4. A surgical suture system kit comprising:
   a laparoscopic port site closure device, a needle and a surgical suture system,
   wherein the laparascopic port site device includes:
   a tubular body,
   an operating stick penetrating through the tubular body,
   wings being opened and closed through an operating stick penetrating through the tubular body to operate the wings by being rotated to push and open the wings and to pull and close the wings by being rotated reversely, the laparoscopic port site closure device being configured such that a surgical suture is threaded through the wings so as to pull the surgical suture out of a body of a patient, and
   wherein the surgical suture device comprises:
   the surgical suture,
   a spiral coil made of a material that is different from a material of the surgical suture and which is connected to each end of the surgical suture for engaging a needle used with the laparoscopic port site closure device so as to be pulled outside of the body of the patient,
   a silicone tube fitted over a junction between the spiral coil and the surgical suture to protect the junction, and
   a ball-shaped stopper integrally provided at each end of the spiral coil configured to engage the needle and prevent the spiral coil from detaching from the surgical suture;
   wherein the surgical suture is folded and received in a case connected to the laparoscopic port site closure device via a removable cartridge that contains both the case and the spiral coils.

* * * * *